(12) United States Patent
Akula et al.

(10) Patent No.: US 9,677,114 B1
(45) Date of Patent: Jun. 13, 2017

(54) METHOD FOR EVALUATING DEGRADATION PATHWAYS FOR PANCREATIN ACTIVE PHARMACEUTICAL AGENTS

(71) Applicant: Scientific Protein Laboratories, LLC, Waunakee, WI (US)

(72) Inventors: Anisha Akula, Madison, WI (US); Yan Wang, Middleton, WI (US)

(73) Assignee: Scientific Protein Laboratories, LLC, Waunakee, WI (US)

( * ) Notice: Subject to any disclaimer, the term of this patent is extended or adjusted under 35 U.S.C. 154(b) by 0 days.

(21) Appl. No.: 13/865,837

(22) Filed: Apr. 18, 2013

Related U.S. Application Data

(60) Provisional application No. 61/635,108, filed on Apr. 18, 2012.

(51) Int. Cl.
   *C12Q 1/44* (2006.01)
   *C12Q 1/37* (2006.01)
   *C12Q 1/40* (2006.01)

(52) U.S. Cl.
   CPC ............... *C12Q 1/44* (2013.01); *C12Q 1/37* (2013.01); *C12Q 1/40* (2013.01)

(58) Field of Classification Search
   CPC ............... C12Q 1/44; C12Q 1/40; C12Q 1/37
   See application file for complete search history.

(56) References Cited

U.S. PATENT DOCUMENTS 7,479,378 B2 * 1/2009 Potthoff et al. ................. 435/23
9,291,630 B1   3/2016 Wezeman et al.

OTHER PUBLICATIONS

Goke et al., Identification of Rat Pancreatic Secretory Proteins after Separation by High-Performance Liquid Chromatography, Pancreas, vol. 3, No. 2, pp. 199-206, 1988.*
Guzetta, Reverse Phase HPLC Basics for LC/MA, An IonSource Tutorial, IonSource, First published Jul. 22, 2001, available online at: www.ionsource.com/ tutorial/chromatography/rphplc.htm.*
Singh et al., Guidance on Conduct of Stress Tests to Determine Inherent Stability of Drugs, Pharmaceutical Technology On-Line, 4 (Apr. 2000) pp. 1-14.*

* cited by examiner

*Primary Examiner* — Karen Cochrane Carlson
*Assistant Examiner* — Jennifer M. H. Tichy
(74) *Attorney, Agent, or Firm* — Reinhart Boerner Van Deuren P.C.

(57) ABSTRACT

Disclosed is a reverse-phase high-performance liquid chromatography based method for evaluating degradation pathways for panctreatin active pharmaceutical ingredients.

11 Claims, 16 Drawing Sheets

Peak Results

| | Name | RT | Area | Height | Elastase Trypsin Ratio | P13P14 Trypsin Ratio | P19P20 Trypsin Ratio | P22 Trypsin Ratio | P23P23 Trypsin Ratio |
|---|---|---|---|---|---|---|---|---|---|
| 1 | Elastase P1 + Elastase P2 | | | | | | | | |
| 2 | P13 + P14 | | | | | | | | |
| 3 | P23 + P24 | | | | | | | | |
| 4 | P22A + P22B | | | | | | | | |
| 5 | Trypsin P2 | 18.487 | 13985 | 1023 | | | | | |
| 6 | Trypsin P3 | 18.899 | 137581 | 7163 | | | | | |
| 7 | Elastase II P1 | 22.900 | | | | | | | |
| 8 | Elastase II P2 | 23.100 | | | | | | | |
| 9 | P13 | 28.500 | | | | | | | |
| 10 | P14 | 29.500 | | | | | | | |
| 11 | P19 + P20 | 33.400 | | | | | | | |
| 12 | P22A | 38.000 | | | | | | | |
| 13 | P22B | 38.500 | | | | | | | |
| 14 | P23 | 40.034 | | | | | | | |
| 15 | P24 | 41.000 | | | | | | | |

Auto-Scaled Chromatogram

Peak Results

| | Name | RT | Area | Height | Elastase Trypsin Ratio | P13P14 Trypsin Ratio | P19P20 Trypsin Ratio | P22 Trypsin Ratio | P23P23 Trypsin Ratio |
|---|---|---|---|---|---|---|---|---|---|
| 1 | Elastase P1 + Elastase P2 | | | | | | | | |
| 2 | P13 + P14 | | | | | | | | |
| 3 | P23 + P24 | | | | | | | | |
| 4 | P22A + P22B | | | | | | | | |
| 5 | Trypsin P2 | 18.470 | 22431 | 1605 | | | | | |
| 6 | Trypsin P3 | 18.893 | 165341 | 8837 | | | | | |
| 7 | Elastase II P1 | 22.900 | | | | | | | |
| 8 | Elastase II P2 | 23.100 | | | | | | | |
| 9 | P13 | 28.500 | | | | | | | |
| 10 | P14 | 29.500 | | | | | | | |
| 11 | P19 + P20 | 33.400 | | | | | | | |
| 12 | P22A | 38.000 | | | | | | | |
| 13 | P22B | 38.500 | | | | | | | |
| 14 | P23 | 40.034 | | | | | | | |
| 15 | P24 | 41.000 | | | | | | | |

Peak Results

| | Name | RT | Area | Height | Elastase Trypsin Ratio | P13P14 Trypsin Ratio | P19P20 Trypsin Ratio | P22 Trypsin Ratio | P23P23 Trypsin Ratio |
|---|---|---|---|---|---|---|---|---|---|
| 1 | Elastase P1 + Elastase P2 | | | | | | | | |
| 2 | P13 + P14 | | | | | | | | |
| 3 | P23 + P24 | | | | | | | | |
| 4 | P22A + P22B | | | | | | | | |
| 5 | Trypsin P2 | 18.480 | 6828 | 559 | | | | | |
| 6 | Trypsin P3 | 18.897 | 81882 | 4288 | | | | | |
| 7 | Elastase II P1 | 22.900 | | | | | | | |
| 8 | Elastase II P2 | 23.100 | | | | | | | |
| 9 | P13 | 28.500 | | | | | | | |
| 10 | P14 | 29.500 | | | | | | | |
| 11 | P19 + P20 | 33.400 | | | | | | | |
| 12 | P22A | 38.000 | | | | | | | |
| 13 | P22B | 38.500 | | | | | | | |
| 14 | P23 | 40.034 | | | | | | | |
| 15 | P24 | 41.000 | | | | | | | |

Peak Results

| | Name | RT | Area | Height | Elastase Trypsin Ratio | P13P14 Trypsin Ratio | P19P20 Trypsin Ratio | P22 Trypsin Ratio | P23P23 Trypsin Ratio |
|---|---|---|---|---|---|---|---|---|---|
| 1 | Trypsin P2 | 18.581 | 69357 | 4376 | | | | | |
| 2 | Trypsin P2 + Trypsin P3 | 18.581 | 208700 | 11553 | 0.343 | 1.104 | 3.253 | 1.032 | 2.746 |
| 3 | Trypsin P3 | 19.044 | 139344 | 7177 | | | | | |
| 4 | Elastase II P1 | 22.990 | | | | | | | |
| 5 | Elastase II P2 | 23.477 | 71556 | 2188 | | | | | |
| 6 | Elastase P1 + Elastase P2 | 23.477 | 71556 | 2188 | | | | | |
| 7 | P13 | 29.013 | 134855 | 3859 | | | | | |
| 8 | P13 + P14 | 29.013 | 230412 | 6837 | | | | | |
| 9 | P14 | 29.946 | 95557 | 2978 | | | | | |
| 10 | P19 + P20 | 33.591 | 678883 | 24434 | | | | | |
| 11 | P22A | 37.945 | 43130 | 2177 | | | | | |
| 12 | P22A + P22B | 37.945 | 215455 | 9221 | | | | | |
| 13 | P22B | 38.347 | 172325 | 7044 | | | | | |
| 14 | P23 + P24 | 40.350 | 573023 | 17177 | | | | | |
| 15 | P23 | 40.350 | 573023 | 17177 | | | | | |
| 16 | P24 | 41.000 | | | | | | | |

Peak Results

| | Name | RT | Area | Height | Elastase Trypsin Ratio | P13P14 Trypsin Ratio | P19P20 Trypsin Ratio | P22 Trypsin Ratio | P23P23 Trypsin Ratio |
|---|---|---|---|---|---|---|---|---|---|
| 1 | P22A + P22B | | | | | | | | |
| 2 | Trypsin P2 | 18.577 | 67850 | 4692 | | | | | |
| 3 | Trypsin P2 + Trypsin P3 | 18.577 | 205465 | 11930 | 0.397 | 0.265 | 0.284 | | 1.065 |
| 4 | Trypsin P3 | 19.023 | 13761 | 7238 | | | | | |
| 5 | Elastase II P1 | 22.990 | | | | | | | |
| 6 | Elastase II P2 | 23.477 | 81610 | 2241 | | | | | |
| 7 | Elastase P1 + Elastase P2 | 23.477 | 81610 | 2241 | | | | | |
| 8 | P14 | 29.667 | 42402 | 921 | | | | | |
| 9 | P13 | 29.817 | 12108 | 810 | | | | | |
| 10 | P13 + P14 | 29.817 | 54510 | 1732 | | | | | |
| 11 | P19 + P20 | 34.004 | 58440 | 1043 | | | | | |
| 12 | P22A | 38.000 | | | | | | | |
| 13 | P22B | 38.500 | | | | | | | |
| 14 | P23 | 40.354 | 21883 | 6121 | | | | | |
| 15 | P23 + P24 | 40.354 | 21883 | 6121 | | | | | |
| 16 | P24 | 41.000 | | | | | | | |

Peak Results

| | Name | RT | Area | Height | Elastase Trypsin Ratio | P13P14 Trypsin Ratio | P19P20 Trypsin Ratio | P22 Trypsin Ratio | P23P23 Trypsin Ratio |
|---|---|---|---|---|---|---|---|---|---|
| 1 | Trypsin P2 | 18.537 | 70474 | 5247 | | | | | |
| 2 | Trypsin P2 + Trypsin P3 | 18.537 | 204896 | 13030 | 0.200 | 0.196 | 0.643 | 0.245 | 1.723 |
| 3 | Trypsin P3 | 18.976 | 134422 | 7783 | | | | | |
| 4 | Elastase II P1 | 22.990 | | | | | | | |
| 5 | Elastase II P2 | 23.344 | 41036 | 909 | | | | | |
| 6 | Elastase P1 + Elastase P2 | 23.344 | 41036 | 909 | | | | | |
| 7 | P13 | 28.865 | 32140 | 1140 | | | | | |
| 8 | P13 + P14 | 28.865 | 40205 | 1720 | | | | | |
| 9 | P14 | 30.467 | 8065 | 580 | | | | | |
| 10 | P19 + P20 | 33.897 | 131728 | 3132 | | | | | |
| 11 | | 34.596 | 46765 | 1607 | | | | | |
| 12 | P22A | 37.777 | 18624 | 767 | | | | | |
| 13 | P22A + P22B | 37.777 | 50170 | 1980 | | | | | |
| 14 | P22B | 38.301 | 31546 | 1214 | | | | | |
| 15 | P23 + P24 | 40.365 | 352937 | 10037 | | | | | |
| 16 | P23 | 40.365 | 352937 | 10037 | | | | | |
| 17 | P24 | 41.000 | | | | | | | |

Auto-Scaled Chromatogram

Peak Results

| | Name | RT | Area | Height | Elastase Trypsin Ratio | P13P14 Trypsin Ratio | P19P20 Trypsin Ratio | P22 Trypsin Ratio | P23P23 Trypsin Ratio |
|---|---|---|---|---|---|---|---|---|---|
| 1 | P13 + P14 | | | | | | | | |
| 2 | Trypsin P2 | 18.588 | 62319 | 3896 | | | | | |
| 3 | Trypsin P2 + Trypsin P3 | 18.588 | 197451 | 10241 | 0.045 | | 0.304 | 0.051 | 0.554 |
| 4 | Trypsin P3 | 19.064 | 135133 | 6345 | | | | | |
| 5 | Elastase II P1 | 22.990 | | | | | | | |
| 6 | Elastase II P2 | 23.504 | 8954 | 414 | | | | | |
| 7 | Elastase P1 + Elastase P2 | 23.504 | 8954 | 414 | | | | | |
| 8 | P13 | 28.896 | | | | | | | |
| 9 | P14 | 29.500 | | | | | | | |
| 10 | P19 + P20 | 33.628 | 60077 | 1125 | | | | | |
| 11 | P22A | 38.000 | | | | | | | |
| 12 | P22B | 38.358 | 10092 | 492 | | | | | |
| 13 | P22A + P22B | 38.358 | 10092 | 492 | | | | | |
| 14 | P23 | 40.354 | 109363 | 4087 | | | | | |
| 15 | P23 + P24 | 40.354 | 109363 | 4087 | | | | | |
| 16 | P24 | 41.000 | | | | | | | |

Peak Results

| | Name | RT | Area | Height | Elastase Trypsin Ratio | P13P14 Trypsin Ratio | P19P20 Trypsin Ratio | P22 Trypsin Ratio | P23P23 Trypsin Ratio |
|---|---|---|---|---|---|---|---|---|---|
| 1 | Trypsin P2 | 18.583 | 64862 | 4232 | | | | | |
| 2 | Trypsin P2 + Trypsin P3 | 18.583 | 200636 | 11381 | 0.373 | 1.157 | 1.559 | 0.690 | 8.148 |
| 3 | Trypsin P3 | 19.061 | 135774 | 7150 | | | | | |
| 4 | Elastase II P1 | 23.088 | 22068 | 1092 | | | | | |
| 5 | Elastase P1 + Elastase P2 | 23.088 | 74860 | 3283 | | | | | |
| 6 | Elastase II P2 | 23.523 | 52792 | 2191 | | | | | |
| 7 | P13 | 29.007 | 167206 | 4722 | | | | | |
| 8 | P13 + P14 | 29.007 | 232171 | 6851 | | | | | |
| 9 | P14 | 29.950 | 64965 | 2129 | | | | | |
| 10 | P19 + P20 | 33.603 | 312805 | 11265 | | | | | |
| 11 | P22A + P22B | 37.915 | 138536 | 6326 | | | | | |
| 12 | P22A | 37.915 | 40655 | 1947 | | | | | |
| 13 | | 38.340 | 40238 | 2710 | | | | | |
| 14 | P22B | 38.635 | 97881 | 4379 | | | | | |
| 15 | P23 | 40.454 | 609057 | 25844 | | | | | |
| 16 | P23 + P24 | 40.454 | 1634838 | 49077 | | | | | |
| 17 | P24 | 41.094 | 1025781 | 23233 | | | | | |

Auto-Scaled Chromatogram

Peak Results

| | Name | RT | Area | Height | Elastase Trypsin Ratio | P13P14 Trypsin Ratio | P19P20 Trypsin Ratio | P22 Trypsin Ratio | P23P23 Trypsin Ratio |
|---|---|---|---|---|---|---|---|---|---|
| 1 | Trypsin P2 | 18.583 | 49769 | 3297 | | | | | |
| 2 | Trypsin P2 + Trypsin P3 | 18.583 | 175810 | 9945 | 0.402 | 1.247 | 1.115 | 0.937 | 2.047 |
| 3 | Trypsin P3 | 19.035 | 126041 | 6648 | | | | | |
| 4 | Elastase II P1 | 23.051 | 21716 | 998 | | | | | |
| 5 | Elastase P1 + Elastase P2 | 23.051 | 70608 | 3087 | | | | | |
| 6 | Elastase II P2 | 23.481 | 48892 | 2089 | | | | | |
| 7 | P13 | 28.995 | 152167 | 4423 | | | | | |
| 8 | P13 + P14 | 28.995 | 219272 | 6285 | | | | | |
| 9 | P14 | 29.941 | 67106 | 1862 | | | | | |
| 10 | P19 + P20 | 33.589 | 196056 | 7606 | | | | | |
| 11 | P22A | 37.905 | 37618 | 1825 | | | | | |
| 12 | P22A + P22B | 37.905 | 164784 | 6608 | | | | | |
| 13 | P22B | 38.637 | 127166 | 4783 | | | | | |
| 14 | P23 + P24 | 40.362 | 359835 | 12102 | | | | | |
| 15 | P23 | 40.362 | 359835 | 12102 | | | | | |
| 16 | P24 | 41.000 | | | | | | | |

FIGURE 13

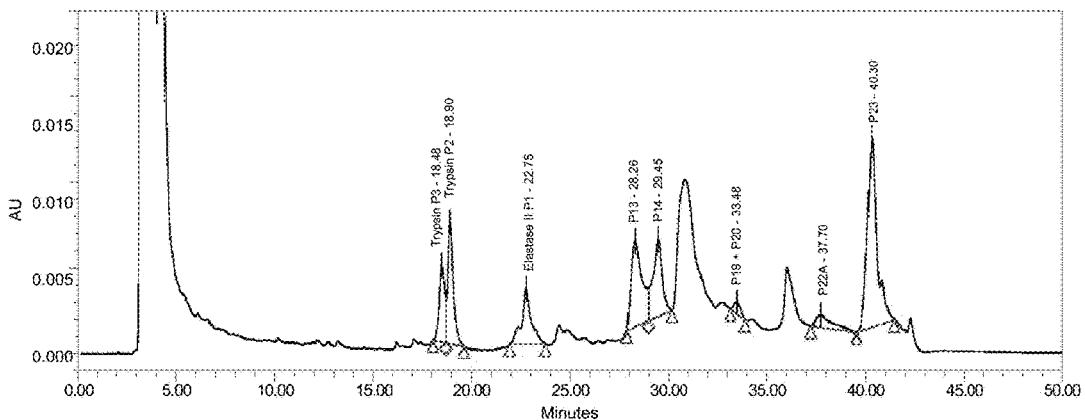

Peak Results

| | Name | RT | Area | Height | Elastase Trypsin Ratio | P13P14 Trypsin Ratio | P19P20 Trypsin Ratio | P22 Trypsin Ratio | P23P23 Trypsin Ratio |
|---|---|---|---|---|---|---|---|---|---|
| 1 | Trypsin P3 | 18.477 | 81263 | 4449 | | | | | |
| 2 | Trypsin P2 | 18.897 | 142706 | 7091 | | | | | |
| 3 | Trypsin P2 + Trypsin P3 | 18.897 | 223969 | 11541 | 0.483 | 1.536 | 0.069 | 0.193 | 1.677 |
| 4 | Elastase II P1 | 22.746 | 108232 | 3200 | | | | | |
| 5 | Elastase P1 + Elastase P2 | 22.746 | 108232 | 3200 | | | | | |
| 6 | Elastase II P2 | 23.400 | | | | | | | |
| 7 | P13 | 28.261 | 194544 | 5016 | | | | | |
| 8 | P13 + P14 | 28.261 | 343958 | 9486 | | | | | |
| 9 | P14 | 29.452 | 149414 | 4470 | | | | | |
| 10 | P19 + P20 | 33.483 | 15375 | 671 | | | | | |
| 11 | P22A | 37.700 | 43313 | 733 | | | | | |
| 12 | P22A + P22B | 37.700 | 43313 | 733 | | | | | |
| 13 | P22B | 38.500 | | | | | | | |
| 14 | P23 + P24 | 40.305 | 375641 | 11028 | | | | | |
| 15 | P23 | 40.305 | 375641 | 11028 | | | | | |
| 16 | P24 | 41.000 | | | | | | | |

Group Peak Results

| | Name | RT | Area | Height | Elstase Trypin Ratio | P13P14 Trypsin Ratio | P19P20 Trypsin Ratio | P22 Trypsin Ratio | P23P23 Trypsin Ratio |
|---|---|---|---|---|---|---|---|---|---|
| 1 | Trypsin P2 + Trypsin P3 | 18.897 | 223969 | 11541 | 0.483 | 1.536 | 0.069 | 0.193 | 1.677 |

Peak Results

| | Name | RT | Area | Height | Elastase Trypsin Ratio | P13P14 Trypsin Ratio | P19P20 Trypsin Ratio | P22 Trypsin Ratio | P23P23 Trypsin Ratio |
|---|---|---|---|---|---|---|---|---|---|
| 1 | Trypsin P3 | 18.464 | 77557 | 4340 | | | | | |
| 2 | Trypsin P2 | 18.879 | 132495 | 6256 | | | | | |
| 3 | Trypsin P2 + Trypsin P3 | 18.879 | 210052 | 10597 | 0.512 | 1.620 | 0.068 | 0.178 | 1.641 |
| 4 | Elastase II P1 | 22.731 | 107572 | 3087 | | | | | |
| 5 | Elastase P1 + Elastase P2 | 22.731 | 107572 | 3087 | | | | | |
| 6 | Elastase II P2 | 23.400 | | | | | | | |
| 7 | P13 | 28.265 | 186188 | 4657 | | | | | |
| 8 | P13 + P14 | 28.265 | 340220 | 8923 | | | | | |
| 9 | P14 | 29.423 | 154031 | 4265 | | | | | |
| 10 | P19 + P20 | 33.459 | 14254 | 625 | | | | | |
| 11 | P22A | 37.661 | 37437 | 637 | | | | | |
| 12 | P22A + P22B | 37.661 | 37437 | 637 | | | | | |
| 13 | P22B | 38.500 | | | | | | | |
| 14 | P23 + P24 | 40.293 | 344728 | 10181 | | | | | |
| 15 | P23 | 40.293 | 344728 | 10181 | | | | | |
| 16 | P24 | 41.000 | | | | | | | |

Peak Results

| | Name | RT | Area | Height | Elastase Trypsin Ratio | P13P14 Trypsin Ratio | P19P20 Trypsin Ratio | P22 Trypsin Ratio | P23P23 Trypsin Ratio |
|---|---|---|---|---|---|---|---|---|---|
| 1 | Trypsin P2 | 18.561 | 51241 | 3426 | | | | | |
| 2 | Trypsin P2 + Trypsin P3 | 18.561 | 180697 | 10184 | 0.242 | 1.240 | 0.810 | 0.859 | 1.752 |
| 3 | Trypsin P3 | 18.999 | 129456 | 6758 | | | | | |
| 4 | Elastase II P1 | 22.897 | 13389 | 669 | | | | | |
| 5 | Elastase P1 + Elastase P2 | 22.897 | 43684 | 1933 | | | | | |
| 6 | Elastase II P2 | 23.361 | 30295 | 1263 | | | | | |
| 7 | P13 | 28.898 | 122282 | 3842 | | | | | |
| 8 | P13 + P14 | 28.898 | 224084 | 7021 | | | | | |
| 9 | P14 | 29.764 | 101802 | 3179 | | | | | |
| 10 | P19 + P20 | 33.518 | 146354 | 5727 | | | | | |
| 11 | P22A | 37.852 | 33138 | 1683 | | | | | |
| 12 | P22A + P22B | 37.852 | 155253 | 6801 | | | | | |
| 13 | P22B | 38.239 | 122114 | 5118 | | | | | |
| 14 | P23 + P24 | 40.359 | 316559 | 11361 | | | | | |
| 15 | P23 | 40.359 | 316559 | 11361 | | | | | |
| 16 | P24 | 41.000 | | | | | | | |

Peak Results

| | Name | RT | Area | Height | Elastase Trypsin Ratio | P13P14 Trypsin Ratio | P19P20 Trypsin Ratio | P22 Trypsin Ratio | P23P23 Trypsin Ratio |
|---|---|---|---|---|---|---|---|---|---|
| 1 | Trypsin P2 | 18.498 | 52132 | 3459 | | | | | |
| 2 | Trypsin P2 + Trypsin P3 | 18.498 | 188546 | 10212 | 0.198 | 1.142 | 0.335 | 0.712 | 1.563 |
| 3 | Trypsin P3 | 18.921 | 136414 | 6753 | | | | | |
| 4 | Elastase II P1 | 22.777 | 11851 | 596 | | | | | |
| 5 | Elastase P1 + Elastase P2 | 22.777 | 37334 | 1683 | | | | | |
| 6 | Elastase II P2 | 23.201 | 25483 | 1087 | | | | | |
| 7 | P13 | 28.655 | 125060 | 3482 | | | | | |
| 8 | P13 + P14 | 28.655 | 215249 | 6369 | | | | | |
| 9 | P14 | 29.514 | 90189 | 2887 | | | | | |
| 10 | | 30.308 | 69193 | 3905 | | | | | |
| 11 | P19 + P20 | 33.468 | 63143 | 2524 | | | | | |
| 12 | P22A | 37.827 | 27432 | 1346 | | | | | |
| 13 | P22A + P22B | 37.827 | 134237 | 5838 | | | | | |
| 14 | P22B | 38.203 | 106805 | 4493 | | | | | |
| 15 | P23 | 40.355 | 294791 | 10998 | | | | | |
| 16 | P23 + P24 | 40.355 | 294791 | 10998 | | | | | |
| 17 | P24 | 41.000 | | | | | | | |

METHOD FOR EVALUATING DEGRADATION PATHWAYS FOR PANCREATIN ACTIVE PHARMACEUTICAL AGENTS

FIELD OF THE INVENTION

The present invention relates generally to a method for evaluating degradation pathways for panctreatin active pharmaceutical ingredients. In particular, the potential degradation pathways of acid, base, oxidation and heat stress conditions are utilized in order to assess the stability-indicating nature of reverse phase high-performance liquid chromatography (RP-HPLC) and enzyme activity methods.

BACKGROUND OF THE INVENTION

Pancreatin is a mixture of several digestive enzymes produced by the exocrine cells of the pancreas. It is composed of amylase, lipase and protease. The pancreas gland produces both endocrine secretions that enter the blood stream and exocrine secretions that enter the duodenum. Whereas the endocrine secretions comprise hormones such as insulin and glucagon, the exocrine secretions to a large part are made up of enzymes necessary for digestion of food in the duodenum.

Without these enzymes (normally produced by the human pancreas), a substantial portion of undigested food simply passes through the digestive tract and provides no nutritional benefit. Pancreatin can be manufactured from the pancreas of either a pig or a cow. Porcine pancreatin juice is closest to that of humans, with high proportions of lipase and alpha-amylase in comparison with other mammals. Therefore, porcine pancreatin is made only from the pancreas of pigs, and is used to treat conditions in which pancreatic secretions are deficient, such as surgical pancreatectomy, pancreatitis and cystic fibrosis. Pancreatin has been claimed to help with food allergies, celiac disease, autoimmune disease, cancer and weight loss. Pancreatin is sometimes called "pancreatic acid", although it is neither a single chemical nor an acid.

Pancreatin enzyme products (PEPs) of porcine or bovine origin have been available in the United States for the treatment of exocrine pancreatic insufficiency (EPI) since before the enactment of the Federal Food, Drug, and Cosmetic Act of 1938 (the Act). With the exception of one PEP approved in 1996, PEPs have been marketed without New Drug Applications (NDAs) and were considered as dietary supplements. In recent years, the use of PEPs however was severely restricted in the US and Europe due to being derived from animal product, with a risk of viral transmission and bioactivity poorly characterized and standardized. The Food and Drug Administration (FDA) considered that an Over The Counter (OTC) monograph would not be sufficient to adequately regulate these drug products and to standardize enzyme bioactivity, safety and effectiveness. The FDA's guidance for the industry requires all pharmaceutical companies marketing pancreatic enzymes for pancreatin deficiency to be approved under New Drug Applications. Since April 2010, PEPs are available by prescription only and only PEPs approved by the FDA remain on the market. Over-the-counter pancreatic enzyme products that are available without a prescription are classified as dietary supplements rather than drugs.

Accordingly, the degradation pathways of pancreatin active pharmaceutical ingredients (API) must be studied. All potential degradation pathways of pancreatin API must be evaluated under various stress conditions.

SUMMARY OF THE INVENTION

In light of the foregoing, it is an object of the present invention to provide a method for evaluating degradation pathways for pancreatin active pharmaceutical ingredients (API). The method comprises a determination of the effectiveness to detect degradation with current analytical techniques (RP-HPLC and enzyme specific activity assay). In such a way, degradation of one or more enzymes in a pancreatin sample is tested using the methods of the invention as described herein. For example, the degradation of amylase, protease, lipase, trypsin, elastase and the like can be tested. Enzyme degradation of any one or more enzymes present in a pancreatin sample is determined by degradation product, specific enzyme activity, or both.

It is another object of the invention to determine conditions that are suitable to degrade a representative sample of pancreatin API relative to the control material used for the study. The method can also evaluate the ability of the current analytical techniques developed for pancreatin to detect changes in the pancreatin material that has been subjected to the stress conditions. The potential degradation pathways of acidic, alkaline, oxidative, and thermal stress conditions are utilized. The objective is to obtain degrees of degradation in pancreatin sample NMT 50% for trypsin and NLT 0% for the rest of the peaks. The analytical techniques used are RP-HPLC analysis and enzyme specific activity assays for some of the proteins (trypsin, elastase, lipase, amylase and protease) found in pancreatin API.

Accordingly, it will be understood by those skilled in the art that one or more aspects of this invention can meet certain objectives, while one or more other aspects can meet certain other objectives. Each objective may not apply equally, in all its respects, to every aspect of this invention. As such, the following objects can be viewed in the alternative with respect to any one aspect of this invention.

Other objects, features, benefits and advantages of the present invention will be apparent from this summary and the following descriptions of certain embodiments, and will be readily apparent to those skilled in the art. Such objects, features, benefits and advantages will be apparent from the above as taken into conjunction with the accompanying examples, data, and all reasonable inferences to be drawn therefrom.

BRIEF DESCRIPTION OF THE DRAWINGS

FIG. 13 is a chromatogram of pancreatin API #1 under stressed oxidative conditions (3% $H_2O_2$; 60 minutes).

DETAILED DESCRIPTION OF THE INVENTION

Figure 1:
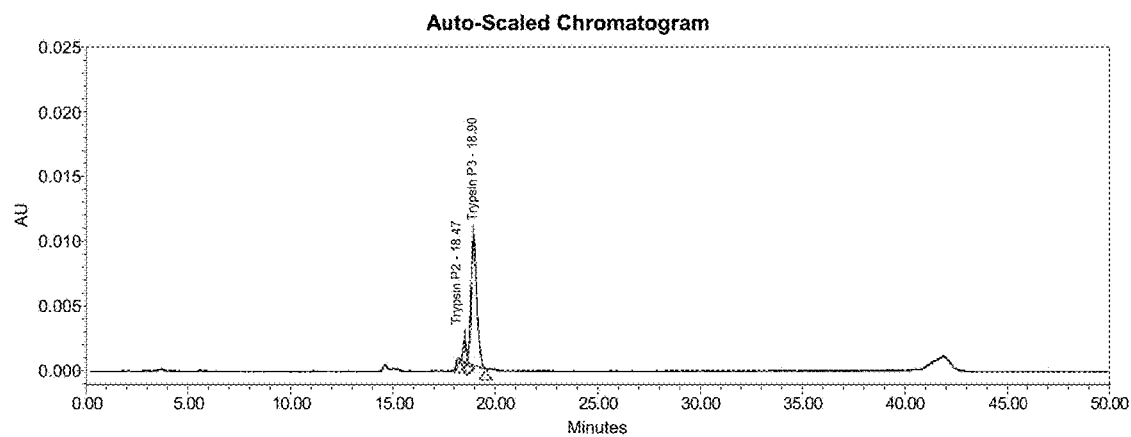
FIG. 1 is a chromatogram of Sigma trypsin (unstressed).

The present invention includes a method to determine conditions that are suitable to degrade a representative sample of pancreatin API up to 30%. The method also determines the ability of current analytical techniques developed to detect changes in a pancreatin protein sample subjected to certain stress conditions. In an embodiment, the potential degradation pathways of acid, alkaline, oxidation and thermal stress conditions are utilized.

Describing certain non-limiting embodiments of the invention, the various stress treatments to which Sigma Trypsin and SPL Pancreatin API sample are subjected to are summarized in Table 1.

TABLE 1

| Stress Type | Stress Treatment | Sample conc. for stress treatment mg/mL | Temp. (° C.) | Time (min) |
|---|---|---|---|---|
| Acid | 0.05N HCl | 25 | RT* | 120 |
| Acid | 0.1N HCl | 25 | RT* | 120 |
| Acid | 1N HCl | 25 | RT* | 120 |
| Alkaline | 0.05N NaOH | 25 | RT* | 10 |
| Alkaline | 0.05N NaOH | 25 | RT* | 60 |
| Oxidation | 3% $H_2O_2$ | 25 | RT* | 60 |
| Oxidation | 3% $H_2O_2$ | 25 | RT* | 120 |
| Thermal | Heating Block | Moist with 0.02 mL PW | 65 | 10 |
| Thermal | Heating Block | Moist with 0.02 mL PW | 65 | 30 |

*RT = Room Temperature (20° C. to 25° C.)

Reverse phase high-performance liquid chromatography (RP-HPLC) is used to separate the proteins in a pancreatin sample. Four different types of stress conditions (acidic, alkaline, thermal and oxidative) are optimized to determine if pancreatin is susceptible to degradation. Sample preparations (before and after stress treatments) and data processing are carried out as described in detail below. The resulting degradation products are detected using certain chromatographic conditions.

The stationary phase for the RP-HPLC methods of the invention may be any stationary phase typically employed for the separation of proteins. In exemplary embodiments, the RP-HPLC column comprises a silica-based stationary phase that is derivatized with an alkyl group. Preferably, the alkyl group is selected from a $C_3$ to $C_{18}$ alkyl group. $C_3$ alkyl groups also may be used as part of the stationary phase. In particular embodiments, the $C_8$ alkyl group is derivatized with a diphenyl group. In other embodiments, the stationary phase comprises a $C_3$ alkyl group that is derivatized with a cyano group. In certain circumstances, it may be possible to employ a stationary phase that comprises a mixture of alkyl groups. A $C_4$ column (Vydac 214MS54, 250×4.6 mm, 5 micron) is preferably used for the separation of pancreatin API proteins. Pancreatin proteins are separated by running a linear-segmented gradient of acetonitrile containing 0.1% trifluoroacetic acid (TFA). The eluted proteins are detected at 280 nm. The relative amounts of individual peaks are quantified using Waters Empower software. Quantification is performed on integrated peak area of individual proteins using a threshold set at 0.5-120, and peak width set at 20-100. The details for RP-HPLC use is found in Table 2 below.

TABLE 2

| HPLC System | Waters Alliance HPLC 2695 with 2487 UV detector |
|---|---|
| Injection volume | 100 μL |
| Column | Vydac $C_4$ column. Cat # 214MS54 (Grace Vydac) (250 mm × 4.60 mm, 5 μm) |
| Column temperature | 40° C. |
| Auto-sampler temperature | 10° C. |
| Sample concentration | 1 mg/mL in 0.1% TFA |
| Mobile phase | Solvent A: 0.1% TFA in PureLab water |
| | Solvent B: 0.1% TFA in Acetonitrile |
| Software | Empower Quickstart |

| Elution conditions | | | |
|---|---|---|---|
| Time (min) | Flow (mL/min) | Solvent A (%) | Solvent B (%) |
| 0 | 1.0 | 85 | 15 |
| 14 | 1.0 | 65 | 35 |
| 28 | 1.0 | 60 | 40 |
| 37 | 1.0 | 50 | 50 |
| 37.5 | 1.2 | 10 | 91 |
| 38.0 | 1.2 | 10 | 90 |
| 39.0 | 1.0 | 85 | 15 |
| 50.0 | 1.0 | 85 | 15 |

Raw data is acquired and processed as peak area. By comparing the peak area of each stressed sample to the peak area of a control (non-stressed) sample in the same run, the amount of degradation caused by each treatment is determined and expressed as % loss degradation. Representative chromatograms are presented in sequential order in Table 3.

TABLE 3

Figure 2:
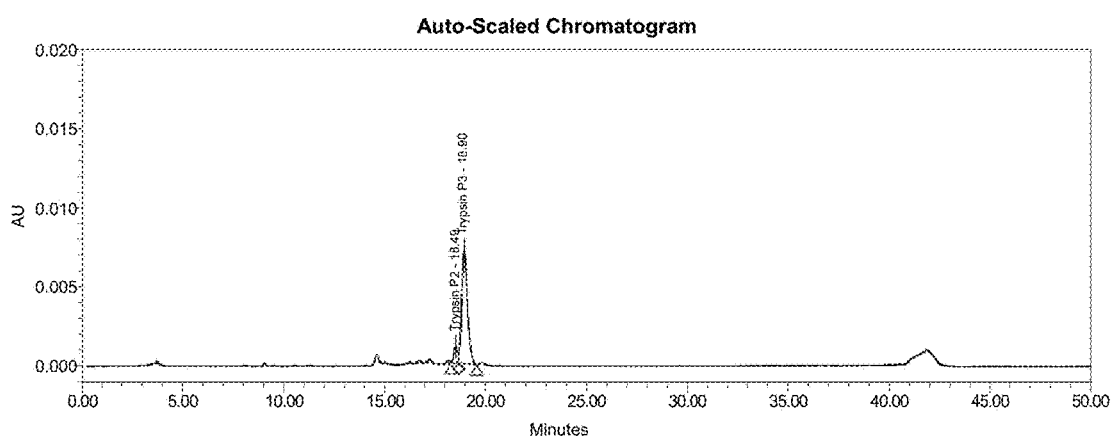
FIG. 2 is a chromatogram of Sigma trypsin under stressed acidic conditions (1 N HCl; 120 minutes).
Figure 3:
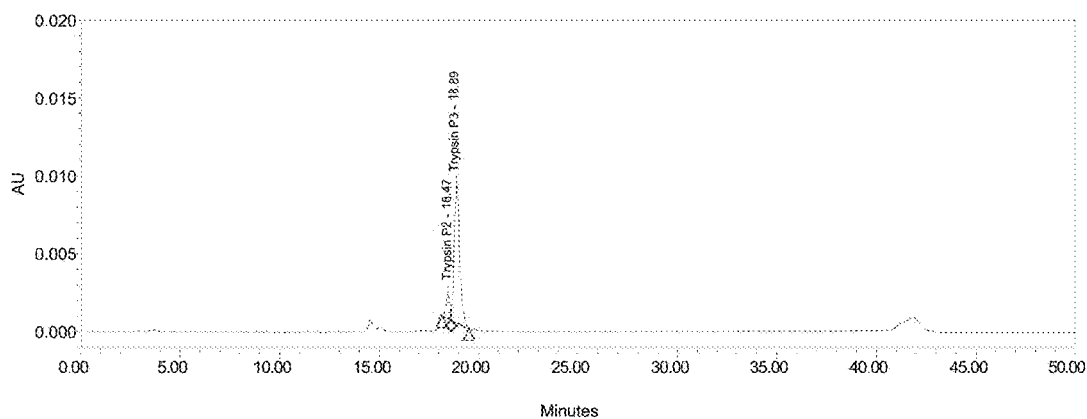
FIG. 3 is a chromatogram of Sigma trypsin under stressed thermal conditions (65° C.; 30 minutes).
Figure 4:
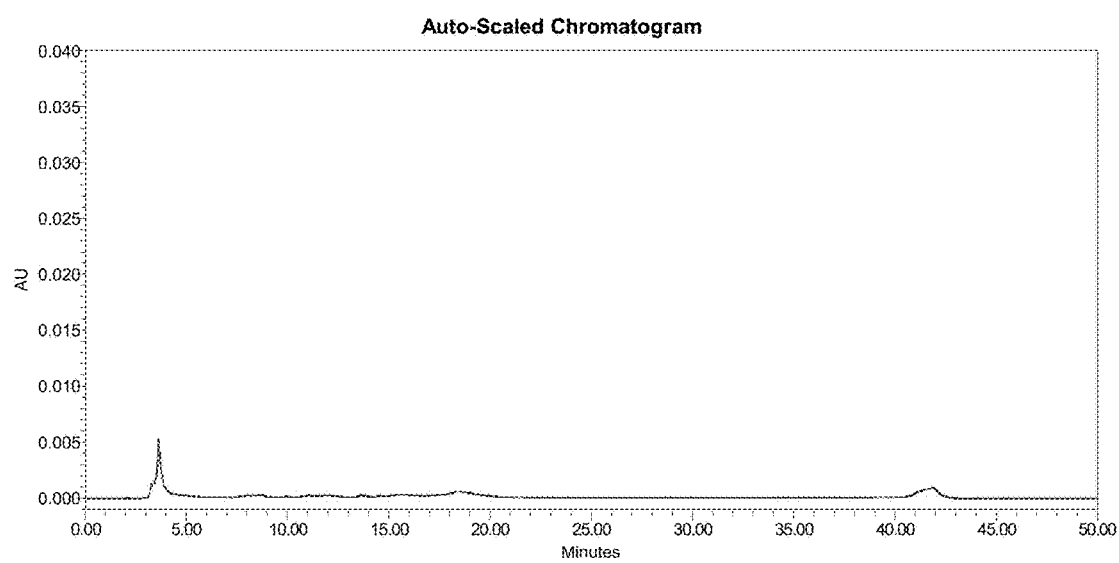
FIG. 4 is a chromatogram of Sigma trypsin under stressed alkaline conditions (0.04 N NaOH; 30 minutes).
Figure 5:
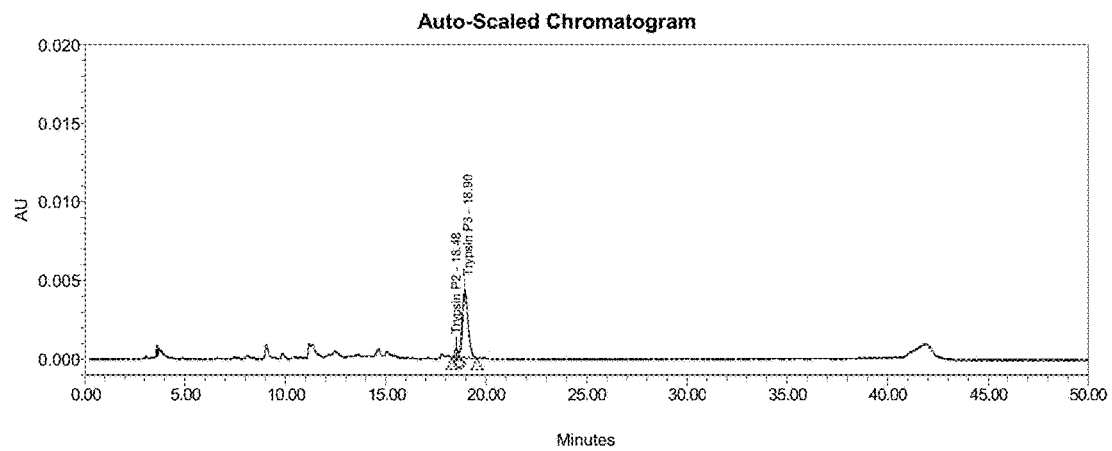
FIG. 5 is a chromatogram of Sigma trypsin under stressed alkaline conditions (0.04 N NaOH; 10 minutes).

| Treatment | Sample Description |
|---|---|
| Control (FIG 1) | Sigma Trypsin (unstressed) |
| Acidic (1N HCl; 2 hrs) (FIG. 2) | Sigma Trypsin |
| Thermal (65 ° C.; 30 min) (FIG. 3) | Sigma Trypsin |
| Alkaline (0.04N NaOH; 30 min) (FIG. 4) | Sigma Trypsin |
| Alkaline (0.04N NaOH; 10 min) (FIG. 5) | (0.04N NaOH; 30 min) |
| Control (FIG. 6) (unstressed) | Pancreatin API Sample # 1 |
| Blank (FIG. 7) | 0.1% TFA in pure water |
| Acidic (0.05N HCl; 2 hrs) (FIG. 8) | Pancreatin API Sample # 1 |

TABLE 3-continued

| Treatment | Sample Description |
| --- | --- |
| Acidic (0.1N HCl; 2 hrs) (FIG. 9) | Pancreatin API Sample # 1 |
| Acidic (1.0N HCl; 2 hrs) (FIG. 10) | Pancreatin API Sample # 1 |
| Alkaline (0.05N NaOH; 10 min) (FIG. 11) | Pancreatin API Sample # 1 |
| Alkaline (0.05N NaOH; 60 min) (FIG. 12) | Pancreatin API Sample # 1 |
| Oxidative (3% H2O2; 60 min) (FIG. 13) | Pancreatin API Sample # 1 |
| Oxidative (3% H2O2; 120 min) (FIG. 14) | Pancreatin API Sample # 1 |
| Thermal (65° C.; 10 min) (FIG.15) | Pancreatin API Sample # 1 |
| Thermal (65° C.; 30 min) (FIG.16) | Pancreatin API Sample # 1 |

% degradation is calculated using the following formula:

$$\% \text{ Degradation} = [\{(A \times B/C) = D\}/(A \times B/C) \times 100\%]$$

A=selected peak area of control (unstressed); B=weight of sample (stress); C=weight of control sample (unstressed); and D=selected peak area of sample (stressed).

Enzymatic activity assays are routinely used to measure a specific active protein in a complex protein mixture. Samples are exposed to four different types of stress conditions (acidic, alkaline, thermal and oxidative) to determine if pancreatin is susceptible to degradation. Sample preparations (before and after stress treatments) and data processing are carried out according to the requirements of each specific protocol. The resulting degradation products are measured for trypsin, elastase, lipase, amylase and protease activity.

In another specific non-limiting example of the invention, trypsin and elastase assays are performed using a Bio-Tek synergy HT multi-detection microplate reader, lipase assay is performed using a Mettler Toledo DL58 titrator, and protease assay is performed using a Spectronic 5 Spectrophotometer.

% degradation is calculated using the following formula:

$$\% \text{ Degradation} = [\{(A \times B/C) - D\}/(A \times B/C) \times 100\%]$$

A=U/ml activity of control (unstressed); B=weight of sample (stress); C=weight of control sample (unstressed); and D=U/ml activity of sample (stressed).

Sigma trypsin (lot #055K7770) standard is used to examine the effects of the stress conditions on trypsin itself, i.e. in the absence of other enzymes.

To establish the method suitability, Sigma porcine trypsin at concentration of 0.04 mg/mL is used initially. The Sigma trypsin profile of degraded peak due to acidic (1.0 N HCl) (FIG. 2), thermal (65° C.) (FIG. 3) and alkaline (0.04 N NaOH) (FIGS. 4 and 5) stress treatments is compared with the control (unstressed) (FIG. 1) trypsin profile. Since alkaline treatment led to higher levels of degradation, further optimization is performed on SPL pancreatin API. The forced degradation results with Sigma porcine trypsin demonstrated that the method is suitable (see Table 4 below). Oxidation treatment is not performed on the Sigma trypsin standard.

TABLE 4

| Stress Treatment | Retention time (Minute) | Average Area | % Area Loss |
| --- | --- | --- | --- |
| Control (unstressed) (FIG. 1) | 18.47 | 208370 | NA |

TABLE 4-continued

| Stress Treatment | Retention time (Minute) | Average Area | % Area Loss |
| --- | --- | --- | --- |
| Acid (1N HCl 2 h) (FIG. 2) | 18.49 | 151566 | 27.6 |
| Alkaline (0.04N NaOH 10 min) (FIG. 3) | 18.48 | 88710 | 57.0 |
| Alkaline (0.04N NaOH 30 min) (FIG. 4) | NA | NA | 100.0 |
| Thermal (65° C. 30 min) (FIG. 5) | 18.47 | 187771 | 10.0 |

All the chromatograms of the pancreatin API of unstressed control sample gave nearly identical profiles. Table 5 summarizes the peaks that are used to determine degradation.

TABLE 5

| Peak # | Retention Time (Minutes) | Peak ID | Peak Name |
| --- | --- | --- | --- |
| 1 | 18-19 | Trypsin-2 & Trypsin -3 | Trypsin (P2 + P3) |
| 2 | 22-23 | Elastase II - 1 and Elastase 11-2 | Elastase II (P2 + P3) |
| 3 | 28-29 | Elastase, Chymotrypsin and Lipase | (P13 + P14) |
| 4 | 33-34 | Amylase and Elastase I | (P19 + P20) |
| 5 | 37-38 | CPA, CPB, Elastase, Amylase etc. | (P22 A + 22 B) |
| 6 | 40-41 | Elastase and Amylase | (P23) |

Figure 6:
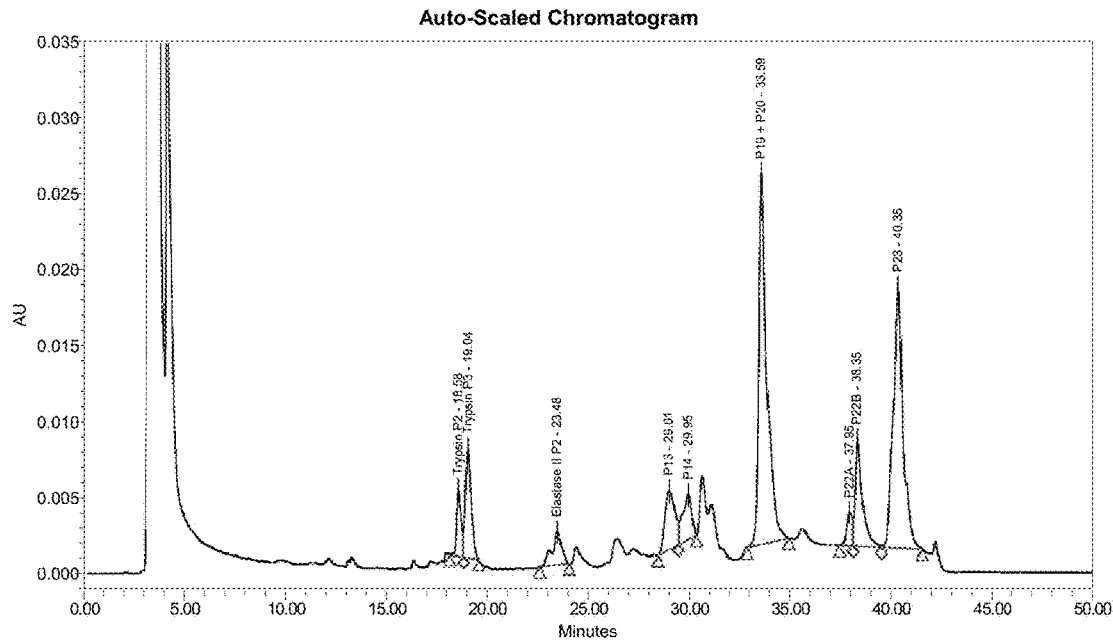
FIG. 6 is a chromatogram of pancreatin API #1 control (unstressed).

These identified peaks are used to determine the percent loss in peak area due to forced degradation. The profiles of the degraded peaks are compared with control (unstressed) peak profiles (FIG. 6). The RP-HPLC protein profiles of degraded samples are different from the control (unstressed) sample profile and each type of stress condition produces different RP-HPLC protein profile. The relative amount of each peak is calculated using an integration threshold of 0.5 to 120 and peak width of 20 to 100. The settings can be adjusted as needed until an appropriate baseline position of the peak is obtained. Table 6 shows the results calculated from control (unstressed) and stressed (only trypsin peak (P2+P3)) replicates using threshold of 10 and a peak width of 100. The maximum % RSD is less than 10% for all the selected peaks (six peaks) of the control sample and for the trypsin peak of stressed samples, indicating that the method is reproducible with precision. The % RSD for degraded samples varies from peak to peak and depends on the stress treatment used.

TABLE 6

| Stress Treatment | Peak ID | Average Retention Time (min) | Average Area | *Number of Replicates | % RSD |
| --- | --- | --- | --- | --- | --- |
| Unstressed | Trypsin (P2 + P3) | 18.68 | 213783 | 48 | 3.1 |
| | Elastase II (P1 + P2) | 23.10 | 74814 | 48 | 4.8 |
| | P13 + P14 | 28.86 | 249872 | 48 | 9.1 |

TABLE 6-continued

| Stress Treatment | Peak ID | Average Retention Time (min) | Average Area | *Number of Replicates | % RSD |
|---|---|---|---|---|---|
| | P19 + P20 | 33.43 | 670961 | 48 | 7.8 |
| | P22A + P22B | 37.90 | 201474 | 48 | 8.6 |
| | P23 | 40.24 | 585175 | 48 | 3.5 |
| Stressed (0.05N HCl; 2 h) | Trypsin (P2 + P3) | 18.58 | 209164 | 6 | 1.7 |
| Stressed (0.1N HCl; 2 h) | Trypsin (P2 + P3) | 18.66 | 209023 | 10 | 7.7 |
| Stressed (1.0N HCl; 2 h) | Trypsin (P2 + P3) | 18.59 | 200420 | 6 | 6.8 |
| Stressed (0.05N NaOH; 10 m) | Trypsin (P2 + P3) | 18.60 | 206833 | 6 | 3.6 |
| Stressed (0.05N NaOH; 60 m) | Trypsin (P2 + P3) | 18.72 | 187419 | 12 | 4.0 |
| Stressed (3% H2O2; 60 m) | Trypsin (P2 + P3) | 18.70 | 222461 | 12 | 4.3 |
| Stressed (3% H2O2; 120 m) | Trypsin (P2 + P3) | 18.73 | 220133 | 9 | 2.9 |
| Stressed (65° C. Thermal; 10 m) | Trypsin (P2 + P3) | 18.76 | 181718 | 6 | 4.2 |
| Stressed (65° C. Thermal; 30 m) | Trypsin (P2 + P3) | 18.67 | 172258 | 12 | 5.2 |

*Replicate -total number of injections in multiple days

Figure 7:
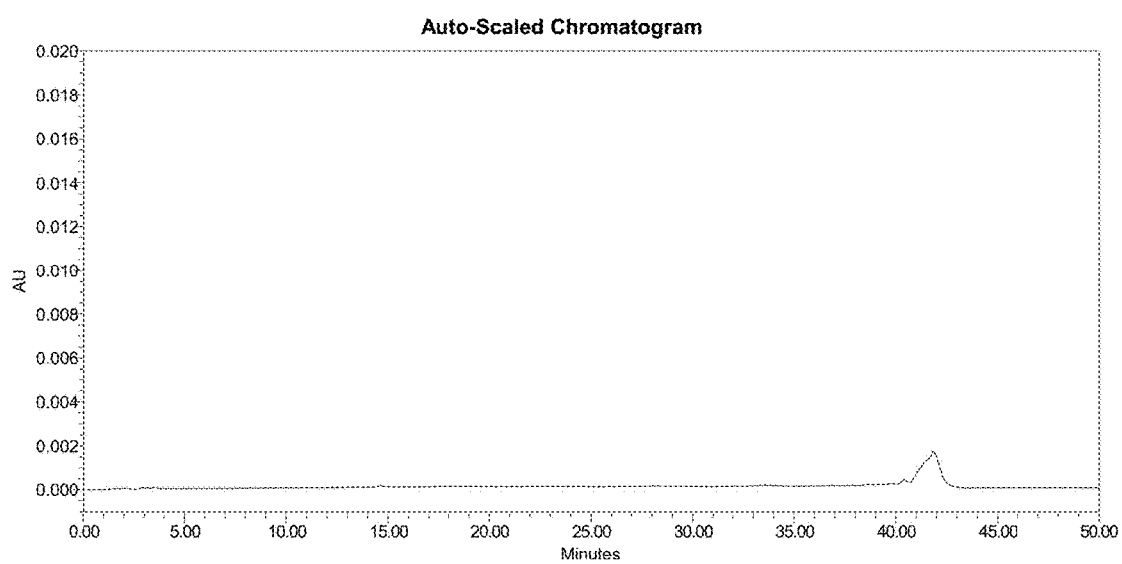
FIG. 7 is a blank chromatogram.

All blanks injected in various runs consistently give profiles showing no significant signals in the 5-50 minutes range and none that could interfere with the peaks of interest (FIG. 7). In all cases, the same initial void peak (4.5 min) and gradient (wash) signals (43-45 min) are visible.

Figure 10:
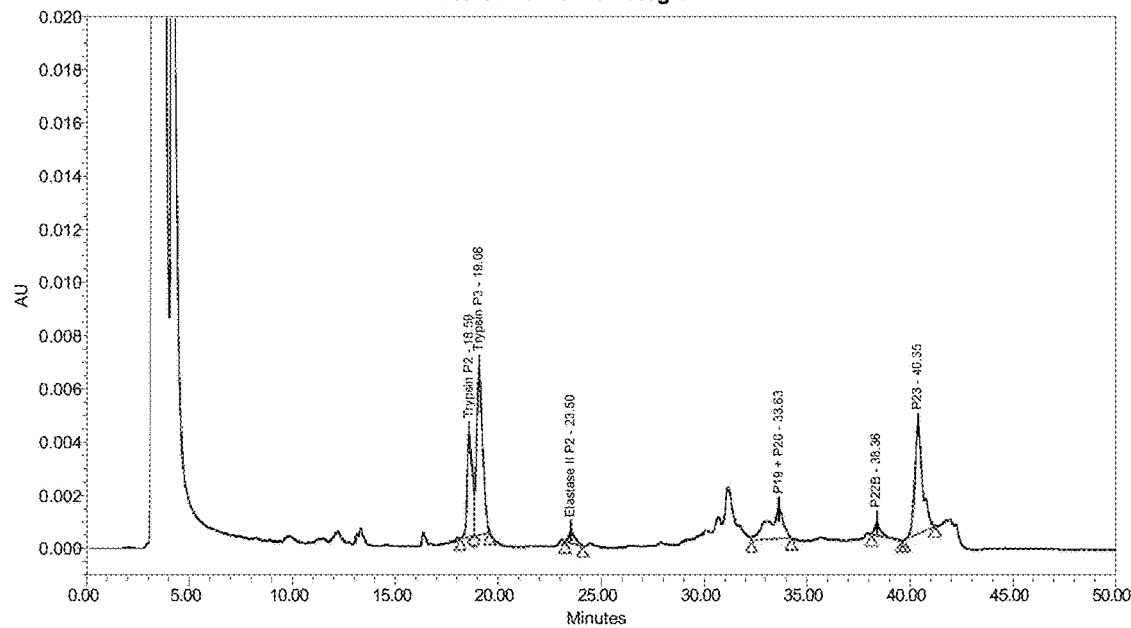
FIG. 10 is a chromatogram of pancreatin API #1 under stressed acidic conditions (1.0 N HCl; 120 minutes).

It is noted during many of the runs that some small peaks are degraded or changed in such a way to affect the integration of the larger peaks. This is seen for trypsin in the Sigma standard and control chromatograms, wherein a valley-to-wally integration is used, resulting in an angled line. In some of the treatments, the integration shows a straighter baseline or a slight angle in the opposite direction (FIG. 10). This change in the baseline for integration is partially responsible for the apparent lack of or increase in peak area. For example, the straighter baseline for trypsin results in more area being included that is not seen using the angled line in the control (FIG. 6).

Acid Treatment

Figure 8:
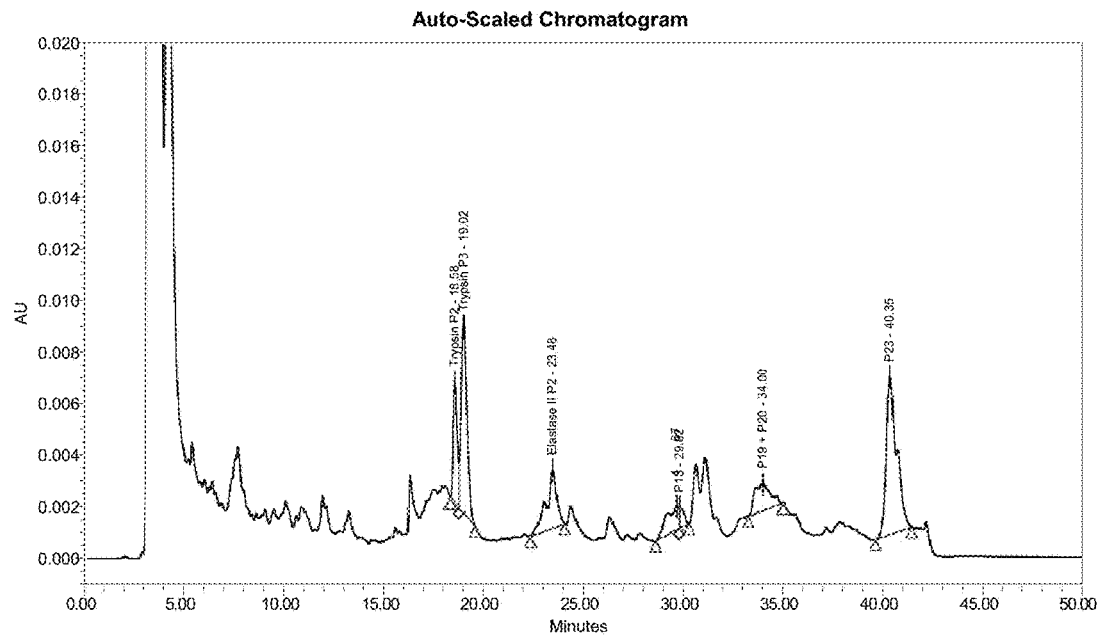
FIG. 8 is a chromatogram of pancreatin API #1 under stressed acidic conditions (0.05 N HCl; 120 minutes).
Figure 9:
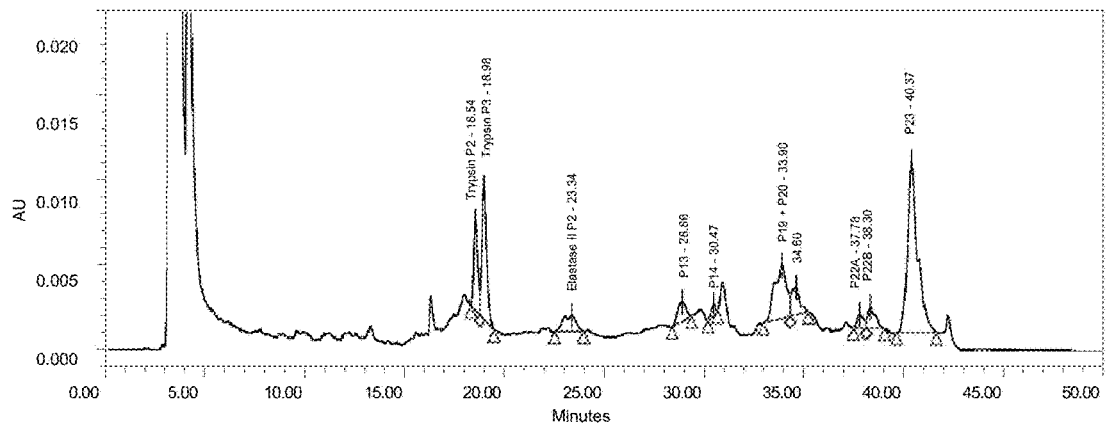
FIG. 9 is a chromatogram of pancreatin API #1 under stressed acidic conditions (0.1N HCl; 120 minutes).

As illustrated in Table 7, when pancreatin is treated with 0.05 N (FIG. 8), 0.1 N (FIG. 9) and 1.0 N HCl (FIG. 10) for 2 hours, trypsin degradation is between 0.05% to 4.3%. However, the elastse II peak (P1+P2) does not lose any area when treated with 0.05 N HCl, whereas acid treatment with 0.1 N and 1 N HCl results in degradation of 49% and 90%, respectively. The negative values reported for the peak (elastase II P1+P2) treated with 0.05 N HCl (weaker condition) correspond to an actual gain in the peak area. This indicates that under these conditions, the actual elastase degradation levels are minimal, or there is another peak underneath due to degradation. The rest of the other peaks [(P13+P14); (P19+P20); (P22A+P22B)] results in degradation levels more than 50% with all three acid concentrations (Table 7). As shown in the chromatograms of FIGS. 8 and 9, the 0.05 N and 0.1 N HCl treated samples show the appearance of numerous signals before 15 minutes, wherein the more hydrophilic (hydrolyzed) peptide fragments elute. These signals are not observed in samples treated with 1 N HCl (FIG. 10).

TABLE 7

| Stress Treatment | Peak ID | Average Peak Area | Average % Area Loss |
|---|---|---|---|
| 0.05N HCl 2 h RT | trypsin (P2 + P3) | 209164 | 0.1 |
| | elastase II (P1+P2) | 97255 | -14.9 |
| | P13+P14 | 74755 | 70.2 |
| | P19 + P20 | 59307 | 91.5 |
| | P22A + P22B | 37609 | 78.9 |
| | P23 | 205252 | 64.6 |
| 0.1N HCl 2 h RT | | 204023 | 1.4 |
| | | 39462 | 49.4 |
| | | 55798 | 75.7 |
| | | 82551 | 89.5 |
| | | 56888 | 79.1 |
| | | 290596 | 51.0 |
| 1.0N HCl 2 h RT | trypsin (P2 + P3) | 200420 | 4.3 |
| | elastase II (P1+P2) | 8928 | 90.0 |
| | P13+P14 | 12894 | 95.2 |
| | P19 + P20 | 46464 | 93.3 |
| | P22A + P22B | 10887 | 94.2 |
| | P23 | 100392 | 82.7 |

Alkaline Treatment

In the alkaline treatment pancreatin chromatogram, the material that elutes beyond 20 minutes in the corresponding control sample (FIG. 6) appears to degrade much less than by the acid treatment. Also, contrary to the acid treatment, no significant signals appear before 15 minutes where the hydrophilic (hydrolyzed) peptide fragments elute.

Figure 11:
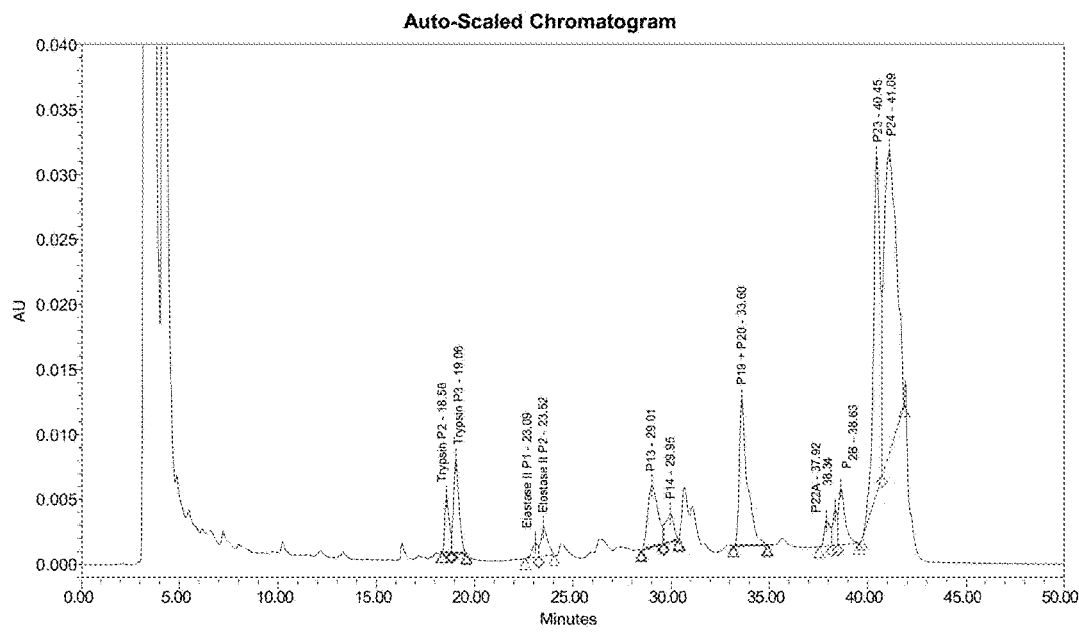
FIG. 11 is a chromatogram of pancreatin API #1 under stressed alkaline conditions (0.05 N NaOH; 10 minutes).
Figure 12:
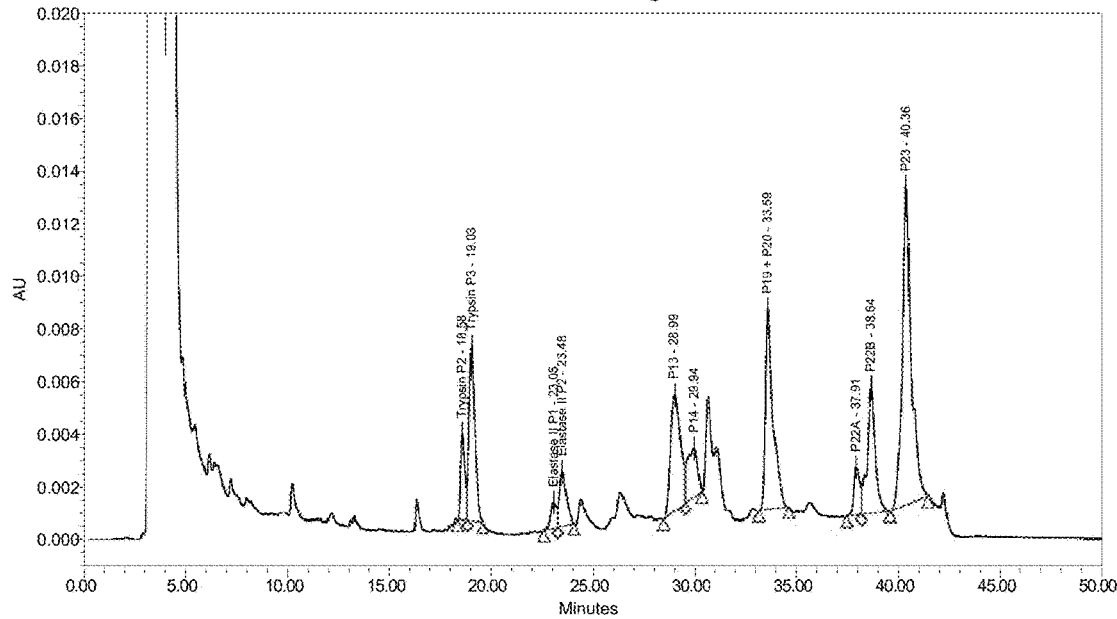
FIG. 12 is a chromatogram of pancreatin API #1 under stressed alkaline conditions (0.05 NaOH; 60 minutes).

As shown in Table 8, when pancreatin API is treated with 0.05 N NaOH for 10 minutes (FIG. 11) and 60 minutes (FIG. 12), trypsin is degraded 1.2% and 10.9%, respectively. However, there is no significant impact on elastase II when treated with 0.05 N NaOH for 10 minutes (FIG. 11). The negative value reported for the elastase II peak (P1+P2) with 0.05 N NaOH for 10 minutes corresponds to an actual gain in the degraded peak area, indicating that the actual elastase II degradation is minimal. Thus, the method is repeated with longer alkaline exposure (0.05 N NaOH for 60 minutes) to increase degradation level for elastase II peak (P1+P2). By increasing the stress treatment period from 10 minutes to 60 minutes (FIG. 12), the desired level of degradation (Table 8) is generated for elastase II.

TABLE 9

| Stress Treatment | Peak ID | Average Area | Average % Area Loss |
|---|---|---|---|
| 0.05N NaOH 10 min RT | Trypsin (P2 + P3) | 206833 | 1.2 |
| | Elastase II (P1 + P2) | 86166 | -4.0 |
| | P13 + P14 | 211454 | 13.6 |
| | P19 + P20 | 282860 | 59.3 |
| | P22A + P22B | 145185 | 13.0 |
| | P23 | 505208 | 12.6 |
| 0.05N NaOH 60 min RT | Trypsin (P2 + P3) | 187419 | 10.9 |
| | Elastase II (P1 + P2) | 77176 | 3.3 |
| | P13 + P14 | 232331 | 5.5 |
| | P19 + P20 | 179005 | 74.0 |
| | P22A + P22B | 156336 | 20.2 |
| | P23 | 354646 | 38.9 |

Oxidation Treatment

Figure 14:
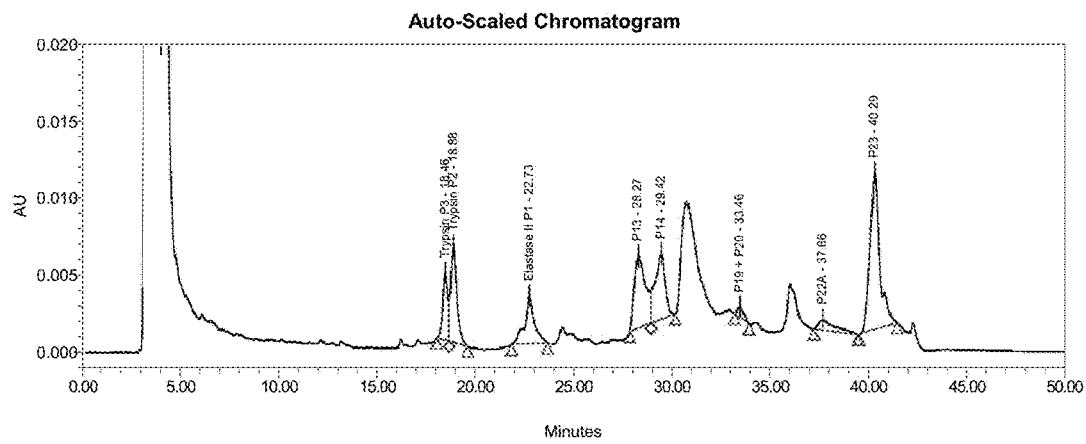
FIG. 14 is a chromatogram of pancreatin API #1 under stressed oxidative conditions (3% $H_2O_2$; 30 minutes).

In the hydrogen peroxide-treated pancreatin sample, the corresponding chromatogram reveals that the amount of material eluting between 20 and 30 minutes does not decrease compared to the unstressed sample, but the overall profile is quite different, as can be seen by comparing FIG. 6 with FIGS. 13 and 14. As shown in Table 9, the negative values reported with the oxidation treatment for 1 hour correspond to an actual gain in the area of the trypsin peak (P2+P3), elastase II (P1+P2) peak and peak (P13+P14). This indicates that under these conditions, the actual degradation levels are minimal. However, due to the complexity of pancreatin sample, some other unidentified and coeluting peaks may have appeared due to the degradation. Thus, the method is repeated with longer exposure to the oxidative conditions (3% $H_2O_2$ for 2 hours) to check if the gain in peak area is due to method imprecision. Comparison of the unstressed pancreatin chroamtogram (FIG. 6) with peroxide-treated pancreatin samples for 1 hour verses 2 hours did not lead to a clear degradation. The peroxide-treated chromatogram for 1 and 2 hours are identical. As reported in Table 9, higher level of degradation due to oxidation treatment is observed only in peak (P19+P20), peak (P22A+P22B) and peak P23.

TABLE 9

| Stress Treatment | Peak ID | Average Area | Average % Area Loss |
|---|---|---|---|
| 3% $H_2O_2$ 60 min RT | Trypsin (P2 + P3) | 222461 | −4.1 |
| | Elastase II (P1 + P2) | 109537 | −28.5 |
| | P13 + P14 | 349507 | −45.1 |
| | P19 + P20 | 20639 | 97.0 |
| | P22A + P22B | 36988 | 81.6 |
| | P23 | 394081 | 29.3 |
| 3% $H_2O_2$ 120 min RT | Trypsin (P2 + P3) | 220133 | −1.7 |
| | Elastase II (P1 + P2) | 73375 | −21.4 |
| | P13 + P14 | 295327 | −18.6 |
| | P19 + P20 | 18110 | 97.5 |
| | P22A + P22B | 38978 | 79.6 |
| | P23 | 395953 | 36.9 |

Thermal Treatment

Figure 15:
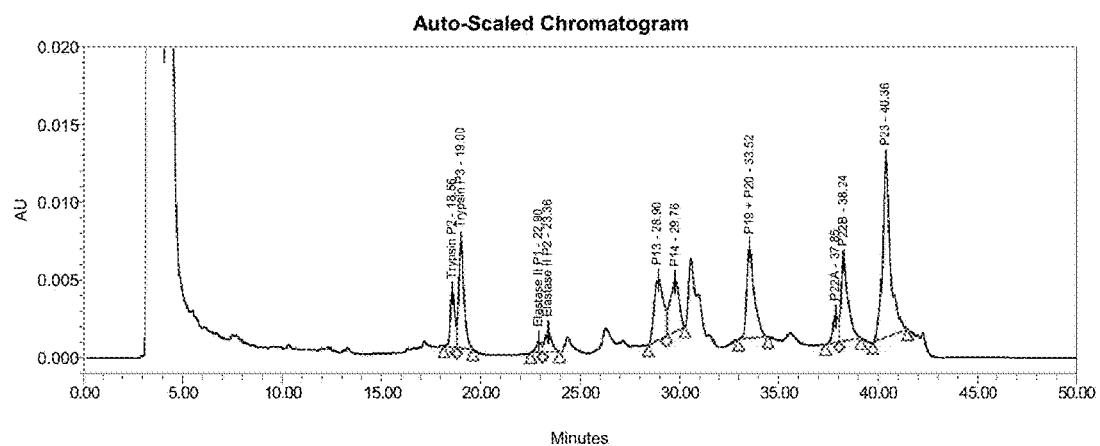
FIG. 15 is a chromatogram of pancreatin API #1 under stressed thermal conditions (65° C.; 10 minutes).
Figure 16:
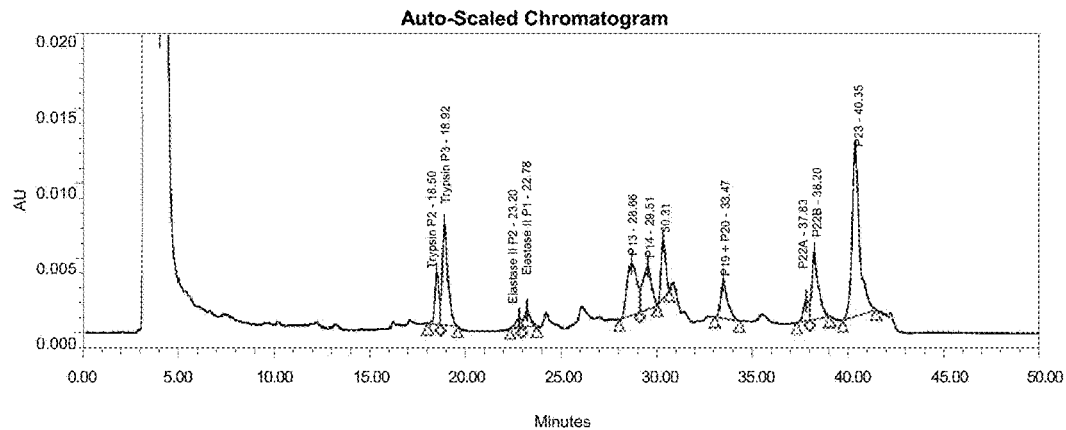
FIG. 16 is a chromatogram of pancreatin API #1 under stressed thermal conditions (65° C.; 30 minutes).

Thermal treatment at 65° C. for 10 minutes leads to increasing levels of degradation for the trypsin peak (P2+P3), up to 15% when compared to acid, alkali and oxidation treatment (FIG. 15). However, peak (P13+P14) generated negative values due to minimal degradation level (Table 10). To check the assignable cause for gain in the area of peak (P13+P14), the experiment is repeated with longer exposure to the thermal conditions (65° C. for 30 minutes). Thermal treatment at 65° C. for 30 minutes results in a degradation level for the trypsin peak (P2+P3) of 20.3%; the elastase II peak (P1+P2) of 54.0%, (P13+P14) of 20.4%, peak (P22A+P22B) of 34.5% and peak (P23) of 48.1% (FIG. 16). As shown in Table 10, a higher level of degradation due to thermal treatment is observed in peak (P19+P20) with 90% loss.

TABLE 10

| Stress Treatment | Peak ID | Average Area | Average % Area Loss |
|---|---|---|---|
| Temperature 65 ° C. 10 min | Trypsin (P2 + P3) | 181718 | 14.9 |
| | Elastase II (P1 + P2) | 48021 | 39.0 |
| | P13 + P14 | 244853 | −11.1 |
| | P19 + P20 | 124487 | 82.1 |
| | P22A + P22B | 165735 | 8.2 |
| | P23 | 331932 | 43.2 |

TABLE 10-continued

| Stress Treatment | Peak ID | Average Area | Average % Area Loss |
|---|---|---|---|
| Temperature 65° C. 30 min | Trypsin (P2 + P3) | 172258 | 20.3 |
| | Elastase II (P1 + P2) | 34161 | 54.0 |
| | P13 + P14 | 194216 | 20.4 |
| | P19 + P20 | 68318 | 90.0 |
| | P22A + P22B | 135865 | 34.5 |
| | P23 | 304212 | 48.1 |

Activity Assay Results

Pancreatin API is a complex mixture consisting of the enzymes trypsin, chymotrypsin, elastase, carboxipeptidase A, carboxipeptidase B, phospholipase, lipase, amylase, lithostathine and cholesterol esterase. This method evaluates the ability of the current analytical techniques developed for pancreatin API to detect changes in the enzymatic activity in a sample that has been subjected to stress conditions. In a non-limiting example, the potential degradation pathways of acid, alkaline, oxidative, and thermal stress conditions are utilized. The detailed sample preparation procedures with and without stress treatment is outlined below. The various stress treatments to which blank, controls and sample are subjected are summarized in Table 11.

TABLE 11

| Stress Type | Stress Treatment | Sample conc. for stress treatment mg/mL | Temperature (° C.) | Time (minutes) |
|---|---|---|---|---|
| Acid | 0.1N HCL | 25 | ambient | 120 |
| Alkaline | 0.05N NaOH | 25 | ambient | 60 |
| Oxidation | 3% $H_2O_2$ | 25 | ambient | 60 |
| Thermal | Heating Block | 50 mg sample moist with 0.02 mL PW | 65 | 30 |

Trypsin Activity Assay

Trypsin activity assay is performed by exposing pancreatin API sample to stress conditions (acidic, alkaline, oxidative and thermal), the assay performed on stressed and unstressed (control) sample. As shown in Table 12, the trypsin activity results for stressed samples generate the desired levels of degradation (between 16.6% and 46.0%).

TABLE 12

| Stress Treatment | Average Trypsin Activity (U/mL) | Average % Loss of Trypsin Activity |
|---|---|---|
| Control (unstressed) | 76.2 | NA |
| Acidic | 63.6 | 16.6 |
| Alkaline | 49.4 | 35.2 |
| Oxidative | 62.2 | 18.4 |
| Thermal | 41.3 | 46.0 |

Elastase Activity Assay

Pancreatin API sample is exposed to optimized stress conditions (acidic, alkaline, oxidative and thermal), the assay performed on stressed and unstressed (control) samples. As shown in Table 13, the elastase activity results for stressed samples treated with acid results in degradation level of 87.3% whereas stressed sample treated with alkaline, oxidative and thermal conditions generated very low levels of degradation (less than 1%), indicating that elastase activity is very sensitive towards acidic stress, yet strong resistance towards alkaline, oxidative and thermal stress.

TABLE 13

| Stress Treatment | Average Elastase Activity (U/mL) | Average % Loss of Elastase Activity |
| --- | --- | --- |
| Control (unstressed) | 0.3312 | NA |
| Acidic | 0.0419 | 87.3 |
| Alkaline | 0.3293 | 0.5 |
| Oxidative | 0.3370 | −1.72 |
| Thermal | 0.3306 | 0.1 |

Lipase Activity Assay

Pancreatin API sample is exposed to optimized stress conditions (acidic, alkaline, oxidative and thermal), the assay performed on stressed and unstressed (control) sample. As shown in Table 14, the lipase activity results for stressed samples treated with acidic conditions generate very high levels of degradation (96.1%) when compared to the results of stressed samples treated with thermal condition (27.1%), indicating that lipase activity is highly susceptible to acidic stress as compared to thermal stress, where lipase activity is moderately stable. As shown in Table 14, the lipase activity results for stressed treated samples with alkaline and oxidative conditions also generate high level of degradation (58.6% with alkaline and 62.3% with oxidation), indicating that lipase activity is unstable with alkaline as well as oxidative stress.

TABLE 14

| Stress Treatment | Lipase Activity (U/mg) | % Loss of Lipase Activity |
| --- | --- | --- |
| Control (unstressed) | 86.2 | NA |
| Acidic | 3.3 | 96.1 |
| Alkaline | 35.7 | 58.6 |
| Oxidative | 32.5 | 62.3 |
| Thermal | 63.0 | 29.1 |

Protease Activity Assay

Pancreatin API sample is exposed to optimized stress conditions (acidic, alkaline, oxidative and thermal), the assay performed on stressed and unstressed (control) sample. The protease activity results for stressed samples generate degradation levels between 5.0% and 57.0%. As shown in Table 15, the protease activity results for stressed samples treated with acidic and alkali conditions result in degradation levels of 56.8% and 46.4%, respectively. Samples exposed to oxidation stress treatment result in degradation level of only 5.0%, indicating that the protease activity is susceptible to acidic and basic stress but has resistance towards oxidative stress. The sample stressed with thermal treatment results in moderate level of degradation (17.5%).

TABLE 15

| Stress Treatment | Protease Activity (U/mg) | % Loss of Protease Activity |
| --- | --- | --- |
| Control (unstressed) | 353.7 | NA |
| Acidic | 153.0 | 56.8 |
| Alkaline | 189.5 | 46.4 |

TABLE 15-continued

| Stress Treatment | Protease Activity (U/mg) | % Loss of Protease Activity |
| --- | --- | --- |
| Oxidative | 336.0 | 5.0 |
| Thermal | 291.8 | 17.5 |

Amylase Activity Assay

Pancreatin API sample is exposed to optimized stress conditions (acidic, alkaline, oxidative and thermal), the assay performed on stressed and unstressed (control) samples. The amylase activity results for stressed samples treated with acid result in degradation level of 90.7%, indicating sensitivity towards acidic treatment. As shown in Table 16, the degradation levels for acidic, alkaline, oxidative and thermal treated samples result in higher levels of degradation compared to the control sample (unstressed), indicating that the amylase activity is susceptible towards all these stress conditions.

TABLE 16

| Stress Treatment | Amylase Activity (U/mg) | % Loss of Amylase Activity |
| --- | --- | --- |
| Control (unstressed) | 357.5 | NA |
| Acidic | 33.0 | 90.8 |
| Alkaline | 166.2 | 53.5 |
| Oxidative | 257.5 | 28.0 |
| Thermal | 239.2 | 33.1 |

EXAMPLES

Materials and Equipment:

Porcine Trypsin: Sigma, Cat. #10303; Pancreatin API sample ID 1208-1423A; 50 mL centrifuge tubes; 15 mL centrifuge tubes; Oakridge Centrifuge tubes, high speed-speed, 35-mL; 10 mL Corning Glass tube with snap caps; 1.5 mL Eppendorf tubes.

Example 1—Preparation of Protein Samples

Sigma Trypsin 25.00±0.25 mg and 50.00±0.05 mg for RP-HPLC of Sigma trypsin, for activity assay and RP-HPLC, respectively, is weighed and dissolved in diluents to get 1 mg/mL stock concentration. A 0.4 mg/mL dilution of trypsin standard is prepared using this stock solution.

Pancreatin API Protein Samples (1 mg/mL)

For RP-HPLC, 30 mg of pancreatin API powder is weighed and put into a 50 mL centrifuge tube. 30 mL of Solvent A is added into the tube, and proteins are extracted by stirring on a stir plate at room temperature for 25 min. An aliquot of the solution (1 mL) is transferred into a micro-centrifuge tube and centrifuged at 13,000 rpm for 10 minutes. The supernatant (800 μL) is carefully removed and used for analysis.

Amount of Samples

1) Sigma trypsin: 50.0±0.1 mg (in 50 mL volumetric flask and 10 mL corning glass tube); 2) pancreatin API Sample ID #1208-1423-A: 50.0±0.1 mg (in 50 mL volumetric flask and 10 mL corning glass tube); 3) trypsin: 25.0±0.25 mg (in 35 mL Nalgene Oakridge high speed centrifuge tube and 10 mL corning glass tube); 4) elastase: 50.0±0.5 mg (in 35 mL Nalgene Oakridge high speed centrifuge tube and 10 mL corning glass tube); 5) lipase: equal to about 2,900 units of lipase activity (in 15 mL sterile centrifuge tube and 10 mL corning glass tube); 6) protease: 100±0.1 mg (in 15 mL centrifuge tube and 10 mL corning glass tube); and 7) amylase: equal to about 7,000 units of amylase activity (in 15 mL centrifuge tube and 10 mL corning glass tube).

Example 2—Acid Impact Study

To obtain 25 mg/mL sample solution, appropriate amounts of 0.05, 0.1, 1.0 N of HCl is added into each of the three samples of protein. The container is stoppered and mixed well (or vortexed for 30 seconds) and the degradation reaction is allowed to take place at room temperature for 2 hours in the dark. 2 mL of 0.05 N, 0.1 N and 1.0 N NaOH is then added to the respective tubes to stop the reaction.

Example 3—Alkaline Impact Study

To obtain 25 mg/mL sample solution, appropriate amount of 0.05 N of NaOH is added into each of two samples of protein. The container is stoppered and mixed well (or vortexed for 30 seconds) and the degradation reaction is allowed to take place at room temperature for 10 minutes (first protein sample) and 60 minutes (second protein sample) in the dark. 2 mL of 0.05 N of HCl is added to both tubes to stop the reaction.

Example 4—Oxidation Impact Study

To obtain 25 mg/mL sample solution, appropriate amount of 3% hydrogen peroxide ($H_2O_2$) is added into each of two samples of protein. The container is stoppered and mixed well (or vortexed for 30 seconds) and the degradation reaction is allowed to take place at room temperature for 60 minutes (first protein sample) and 120 minutes (second protein sample) in the dark.

Example 5—Thermal Impact Study 0.8% moisture is added to each of two samples of protein. The samples are subsequently placed in a thermal-block set at 65° C. to start the degradation reaction. One tube is left in the thermal-block for 10 minutes, the other for 30 minutes. The tubes are then removed (after 10 and 30 minutes, respectively) and cooled to room temperature.

The degradation HPLC studies of Sigma Trypsin reveal adequate levels of degradation while producing a relatively simple chromatographic profile. Overall, chromatographic profiles have strong similarities with those of the corresponding unstressed samples. Further, the various degradation studies of the pancreatin API sample reveal differing levels of degradation dependent on the specific proteins by HPLC and enzymatic assay (see the tables above).

The chromatograms of pancreatin API sample ID#1208-1423A show degradedation with acidic, alkali, hydrogen peroxide and thermal treatment, the complex groups of signals beyond 22 minutes decrease while numerous new signals of varying intensity appear before 15 minutes, reflecting the break down of enzymes into more hydrophilic amino acids and peptide fragments.

The trypsin peak (P2+P3) remaines relatively unchanged after most of the stress treatments in comparison to the other peaks. The % RSD of trypsin peak (P2+P3) area is less than 15% in each stress treatment. This demonstrates the precision of the instrument used. The elastse II (P1+P2) peak, (P13+P14) peak, (P19+P20) peak and (P23) peak have higher % RSD (between 20 and 80%) that could be do to inteference of other unidentified peaks lying underneath as well as integration artifacts (data not presented in this report). The enzymatic activity assay methods measure the change in the pancreatin material subjected to the stressed conditions.

The present study demonstrates the ability of the current analytical techniques used for pancreatin to detect changes in the pancreatin material when subjected to stress conditions. The mechanism and the chromatographic consequences of the inter-conversion between the various proteins and their degradation products is not well understood.

The disclosures of all articles and references, including patents, are incorporated herein by reference. The invention and the manner and process of making and using it are now described in such full, clear, concise and exact terms as to enable any person skilled in the art to which it pertains, to make and use the same. All references cited in this specification are incorporated herein by reference. It is to be understood that the foregoing describes preferred embodiments of the present invention and that modifications may be made therein without departing from the spirit or scope of the present invention.

What is claimed is:

1. A method of determining degradation of one or more proteins in a pancreatin API sample comprising the steps of:
    a) providing independently a first and second pancreatin API sample in solution, wherein the second pancreatin API sample is a pancreatin API control sample;
    b) providing independently a first and second reference sample in solution, wherein the first ad second reference samples comprise a reference enzyme in the absence of other enzymes, and wherein the second reference sample is a reference control sample;
    c) subjecting the first pancreatin API sample and the first reference sample to a stress condition;
    d) performing reverse-phase high performance liquid chromatography (RP-HPLC) on the subjected pancreatin API sample, the pancreatin API control sample, the subjected reference sample, and the reference control sample individually to afford first, second, third, and fourth results, respectively;
    e) comparing the first results with the second results to determine a pancreatin API degradation of the one or more proteins in the subjected pancreatin API sample, wherein the pancreatic API degradation is expressed as % loss degradation;
    f) comparing the third results with the fourth results to determine a reference sample degradation of the reference enzyme in the subjected reference sample, wherein the reference sample degradation is expressed as % loss degradation; and
    g) comparing the pancreatin API degradation to the reference sample degradation to indicate the capability of the method to reveal the changes in the pancreatin API due to the stress condition,
    wherein the stress condition is selected from the group consisting of acidic, basic, oxidative ad thermal, each stress condition making the subjected sample susceptible to degradation of the one or more proteins therein.

2. The method according to claim 1 further comprising conducting an enzymatic activity test for an enzyme on the first and second pancreatin API samples and the first and second reference samples to determine a difference in enzymatic activity, if any, for the enzyme, wherein the enzyme is selected from the group consisting of trypsin, elastase, lipase, protease and amylase.

3. The method according to claim 1 wherein the RP-HPLC has a stationary phase which is a $C_4$ derivatized column.

4. The method according to claim 3 wherein the RP-HPLC has a mobile phase which is a linear-segmented gradient of acetonitrile containing 0.1% trifluoroacetic acid (TFA).

5. The method according to claim 3 wherein the RP-HPLC has a mobile phase which is a 0.1% trifluoroacetic acid solution in water.

6. The method according to claim 3 wherein the oxidative stress condition comprises treating the first pancreatin API sample with hydrogen peroxide.

7. The method according to claim 3 wherein the acidic stress condition comprises treating the first pancreatin API sample and the first reference control sample with an aqueous solution of hydrochloric acid.

8. The method according to claim 3 wherein the basic stress condition comprises treating the first pancreatin API sample and the first reference control sample with an aqueous solution of sodium hydroxide.

9. The method according to claim 1, wherein first reference enzyme is a protease.

10. The method of claim 9, wherein the protease is selected from the group consisting of trypsin, chymotrypsin, elastase, lipase, carboxypeptidase-A (CPA), and carboxypeptidase-B (CPB).

11. The method according to claim 3, wherein the RP-HPLC has a detection wavelength of 280 nm.

* * * * *